US005395506A

United States Patent [19]
Duce et al.

[11] Patent Number: 5,395,506
[45] Date of Patent: Mar. 7, 1995

[54] EXHAUST SENSOR INCLUDING A COMPOSITE TILE SENSING ELEMENT AND METHODS OF MAKING THE SAME

[75] Inventors: Richard W. Duce, Flushing; David B. Quinn, Grand Blanc, both of Mich.

[73] Assignee: General Motors Corporation, Detroit, Mich.

[21] Appl. No.: 281,819

[22] Filed: Jul. 28, 1994

Related U.S. Application Data

[62] Division of Ser. No. 196,863, Feb. 15, 1994.

[51] Int. Cl.$^6$ ............................................. G01N 27/26
[52] U.S. Cl. ................................. 204/426; 204/429; 204/427; 204/424; 204/400
[58] Field of Search ............... 204/421, 424, 425, 426, 204/427, 429

[56] References Cited

U.S. PATENT DOCUMENTS

| | | | |
|---|---|---|---|
| 4,282,080 | 8/1981 | Muller et al. | 204/195 S |
| 4,462,891 | 7/1984 | Lawless | 204/427 |
| 4,559,126 | 12/1985 | Mase et al. | 204/425 |
| 4,574,042 | 3/1986 | Shiraishi | 204/429 |
| 4,639,305 | 1/1987 | Shibata et al. | 204/426 |
| 4,655,901 | 4/1987 | Mase et al. | 204/426 |
| 4,776,943 | 10/1988 | Kitahara | 204/427 |
| 4,980,044 | 12/1990 | Ker | 204/426 |
| 5,075,139 | 12/1991 | Crumbach et al. | 427/286 |

FOREIGN PATENT DOCUMENTS 0148622 7/1985 European Pat. Off. .

*Primary Examiner*—John Niebling
*Assistant Examiner*—Bruce F. Bell
*Attorney, Agent, or Firm*—Cary W. Brooks

[57] ABSTRACT

An exhaust sensor having a substrate including first and second portions, the first portion comprising a dielectric material, the second portion comprising an electrolyte material and a transition zone interposed between the first and second portions. The transition zone includes an increasing concentration of the dielectric material in the direction of the first portion of the substrate and an increasing concentration of the electrolyte material in a direction towards the second portion of the substrate. The invention also includes a method of making such an exhaust sensor substrate including the steps of co-depositing first and second amenable compositions, the first composition comprising a dielectric material and the second composition comprising an electrolyte material. The co-deposited compositions are fired together to form the substrate having first, second and transition portions as described above. The two compositions may be co-deposited as a slurry and spread over a substrate using a partition doctor blade to form a very thin tape of a dielectric material and an electrolyte material. The two compositions may be co-deposited by feeding the compositions side by side through a compaction press to form a single tape having a first dielectric portion and a second electrolyte portion.

3 Claims, 3 Drawing Sheets

EXHAUST SENSOR INCLUDING A COMPOSITE TILE SENSING ELEMENT AND METHODS OF MAKING THE SAME

This is a division of application Ser. No. 08/196,863, filed on Feb. 15, 1994.

FIELD OF THE INVENTION

This invention relates to exhaust sensors, and more particularly to an exhaust sensor having a composite tile sensing element.

BACKGROUND OF THE INVENTION

A known method of making a flat ceramic tile substrate is "roll compaction pressing." In this method ceramic powder is placed in a hopper and is continuously fed between two rollers rotating in opposite directions to form a tape. Only one powder material is loaded into the roll compaction press at one time. After pressing, the tape is cleaned and cut into tiles of various sizes for a particular process or component. However, it was not heretofore known if such a process has been used in making an automotive exhaust sensor.

Two flat zirconia tile substrates may be utilized to make an exhaust sensor. One tile will have platinum electrodes printed on opposite faces and will be the sensor tile. The other tile will have a dielectric film printed on one side and a heater pattern printed over it. This tile will be the heater tile. The dielectric is printed on the one side of the heater tile to prevent electrical shorting from the heater to the sensor. On the inside of the heater tile an air reference slot is made. The two tiles will be laminated together in a process using heat and pressure to form a tile that has a multiple of sensor elements on it.

However, the use of zirconia for the sensor substrates is costly. More economical materials such as alumina have been utilized in conjunction with zirconia. U.S. Pat. No. 4,574,042 discloses a gas analyzing apparatus including an alumina substrate and a solid zirconia electrolyte disk loosely mounted in a circular groove provided near one end of the alumina substrate and held in place by inserting a platinum O-ring between the alumina substrate and the zirconia disk. Such devices are difficult to make and suffer from thermal expansion stresses due to the difference in thermal coefficient of expansion of alumina and zirconia. There are also more suitable substrate materials that have superior thermal and mechanical properties such as alumina.

Moreover, the use of a thin dielectric coating or tape has been proven to be insufficient to prevent electrical shorting. Any porosity or microcracking in the coating ultimately leads to shorting of the device, particularly when using a braze to obtain interconnection to the substrate. Zirconia being conductive at elevated temperatures, can lead to shorting, again particularly when using a braze to obtain interconnection to the substrate.

Substrates made from zirconia are generally weak and have poor thermal shock resistance. They can also exhibit mechanical degradation due to phase transformations if the chemistry, grain size, and sintering conditions are not explicitly controlled.

Zirconia is also a difficult material to process into tape. Special care and preparation of the material is required in order to form the material into a usable tape. Much less care and attention is required of alternate materials such as alumina. This also has an impact on the cost of both equipment and manpower to produce tape.

The present invention overcomes the above disadvantages of the prior art.

SUMMARY OF THE INVENTION

The invention includes an exhaust sensor having a substrate including first and second portions, the first portion comprising a dielectric material, the second portion comprising an electrolyte material. Interposed between the first and second portions is a transition zone, including an increasing concentration of the dielectric material in the direction of the first portion of the substrate and an increasing concentration of the electrolyte material in a direction towards the second portion of the substrate. The invention also includes a method of making such an exhaust sensor substrate including the steps of co-depositing first and second amenable compositions, the first composition comprising a dielectric material and the second composition comprising an electrolyte material. The co-deposited compositions are fired together to form the substrate having first, second and third portions as described above. The two compositions may be co-deposited as a slurry and spread over a substrate using a partitioned doctor blade to form a very thin tape of a dielectric material and an electrolyte material. The two compositions may be co-deposited by feeding the compositions side by side through a compaction press to form a single tape having a first dielectric portion and a second electrolyte portion. In such a process the first composition includes the dielectric material and a binder, and the second composition includes the electrolyte material and a binder. The first and second compositions may be placed in hoppers which are positioned to deliver the compositions to the compaction press in a side by side arrangement.

The invention provides for a planar sensing substrate for use in an exhaust sensor which includes zirconia as the sensing member and is featured only at the end of the device. Placement of the zirconia material at only the tip allows for maximum thickness of a dielectric such as alumina for the remainder of the device. This eliminates the possibility of a short condition between the sensor electrodes and heater leads of the device.

It is also desirable to use a substrate material which has higher mechanical strength, higher elastic modulus, greater thermal shock resistance, has a predictable and more controllable thermal expansion behavior. The substrate is stable over the range of temperatures and environmental conditions within an exhaust system. A substrate with these improved physical properties produces a more robust substrate for this application and environment. A substrate material such as alumina also provides for low cost in comparison to zirconia and requires less processing to form a substrate.

These and other objects, features and advantages of the present invention will be apparent from the following brief description of the drawings, detailed description and appended claims and drawings.

DETAILED DESCRIPTION

A flat plate automotive exhaust sensor operates analogous to a conventional conical-shaped exhaust sensor, such that a first porous catalytic electrode is exposed to the exhaust gases from a combustion engine, while a second porous catalytic electrode, which is disposed across a solid electrolyte substrate from the first electrode, is exposed to a reference gas. The resulting galvanic potential between the two electrodes is then measured and is indicative of the exhaust gas concentration. The difference between the two types of sensors is that the flat plate element, i.e., the solid electrolyte layer, reference and measurement electrodes and optionally heater element, are all provided as flat components so as to form a layered planar structure.

Figure 1:
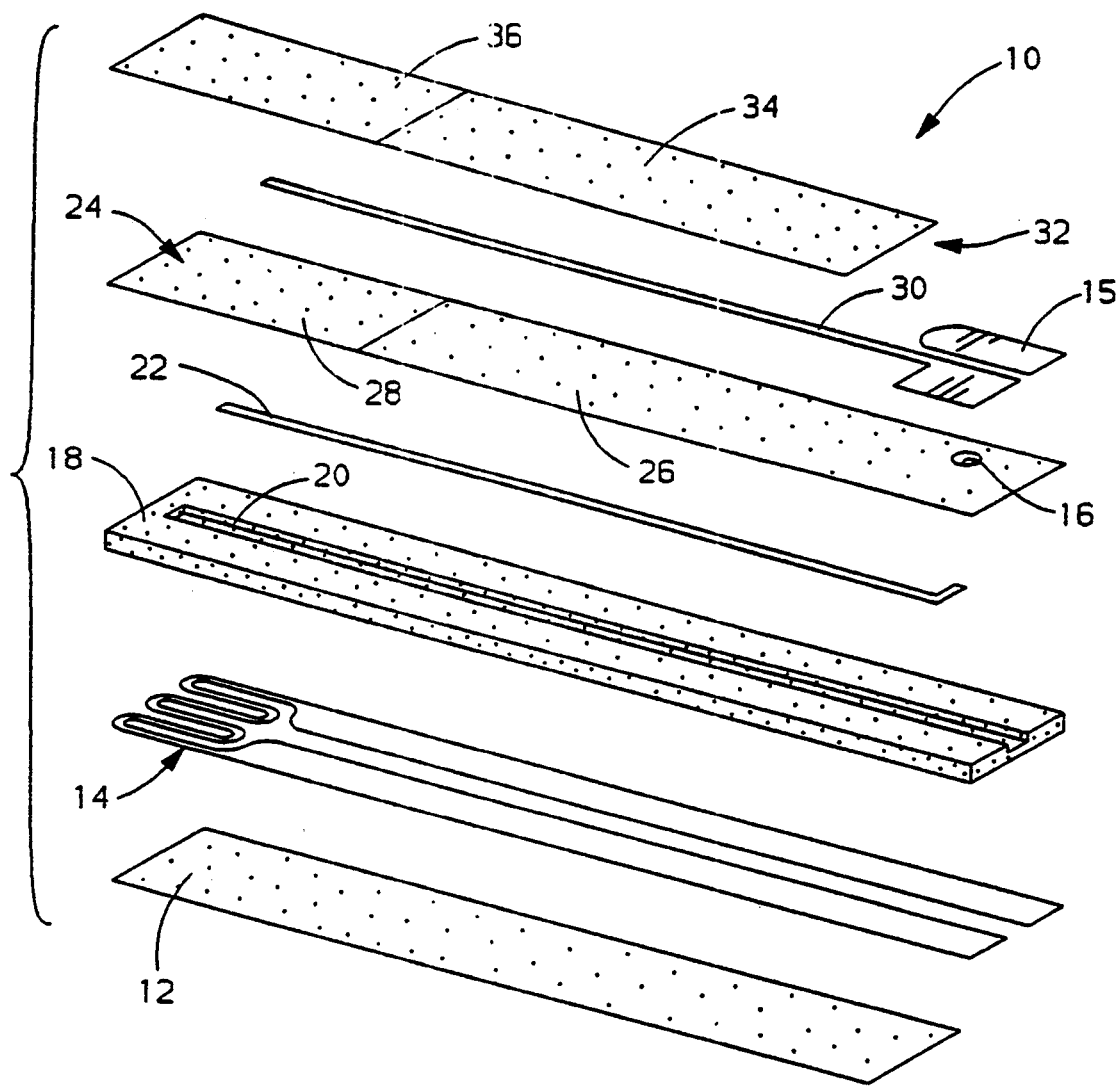
FIG. 1 is an exploded view of a flat plate exhaust sensor including a co-cast composite tape according to the present invention.

FIG. 1 illustrates an exhaust sensor 10 according to the present invention including, an overlapping relationship, the following elements: a heater dielectric protective tape 12; a printed heater 14; an alumina substrate 18 including an air reference channel 20 formed therein; an inner electrode 22 printed on one side of a co-cast composite tape 24 including a dielectric portion 26 and an electrolyte body portion 28; an outer electrode 30 and sensor pads printed on the other side of the co-cast composite tape; and a protective outer tape 32 including a dense alumina portion 34 and a porous alumina portion 36 overlying the electrolyte body portion 28 of the composite tape 32. The tape 24 has a hole 16 formed therein to provide contact between pad 15 and inner electrode 22.

Figure 2:
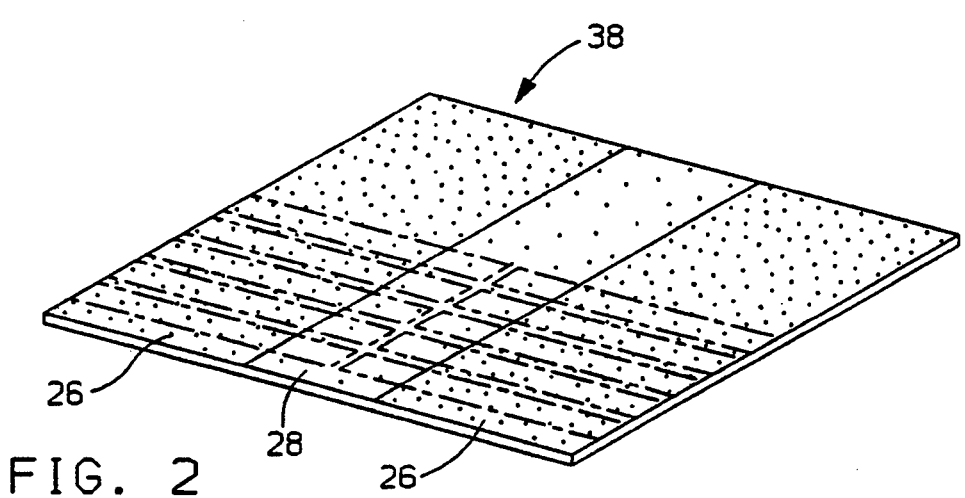
FIG. 2 illustrates an exhaust sensor substrate having a first dielectric portion, a transitional zone and a second electrolyte portion according to the present invention.
Figure 3A:
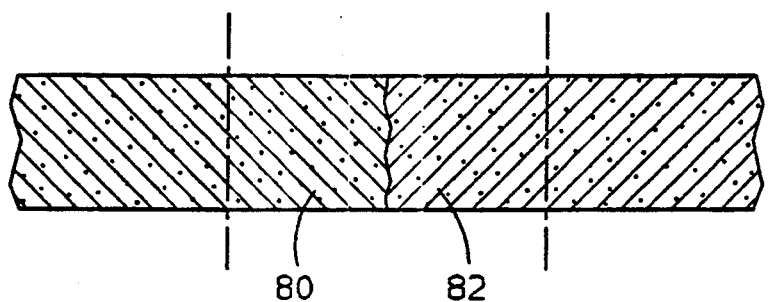
FIG. 3a is an enlarged, partial view of a co-casted dielectric and electrolyte material before the dielectric and electrolyte materials are co-mingled according to the present invention.
Figure 3B:
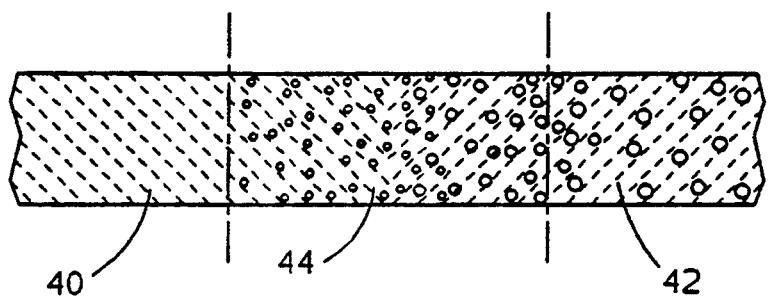
FIG. 3b is an enlarged, partial view of a co-casted dielectric and electrolyte material after a portion of the dielectric and electrolyte materials have been co-mingled according to the present invention.

FIG. 2 illustrates a co-casted composite substrate 38 or tile according to the present invention from which a plurality of individual sensor composite elements are cut along the dotted line. Each element includes first 26 and second 28 portions. The first portion 26 is a dielectric material such as alumina and the second portion 28 is an electrolyte material such as zirconia. FIG. 3a is an enlarged, partial view of a co-casted dielectric material 80 and an electrolyte material 82 just after depositing a dielectric composition and an electrolyte composition and before the compositions co-mingle according to the present invention. FIG. 3b is an enlarged, partial view of co-casted dielectric and electrolyte compositions after they have been co-mingled according to the present invention. The co-mingling step forms a transition zone 44 at the interface between the two portions which comprises an increasing gradient concentration of dielectric material in the direction towards the first portion 40 (dielectric portion) of the substrate, and an increasing gradient concentration of an electrolyte material in the direction towards the second portion 42 (electrolyte portion) of the substrate. The transition zone does not provide for a sharp interface between the dielectric and electrolyte portions of the substrate such as that which might be present when a slurry of electrolyte body is deposited adjacent to a previously fired alumina substrate, and the electrolyte slurry and alumina substrate are co-fired together to make a single substrate. In such case, the interface between the electrolyte body and the alumina substrate has at most a volume percent of the electrolyte body corresponding to the porosity of the alumina substrate. That is, for an alumina substrate having a porosity of 20 percent, the concentration of the electrolyte material at the interface is at most 80 percent alumina by volume and 20 percent electrolyte material. This invention includes a transition zone including a gradient concentration of electrolyte body ranging from 0 percent to 100 percent; and of a dielectric material ranging from 100 percent down to 0 percent. The length of the transition zone may vary, but preferably is about one-tenth of an inch or less.

The transition zone 44 also acts to reduce thermal and mechanical stresses between the dielectric and electrolyte portions of the substrate. Due to the gradient that is formed within the transition zone comprised of the dielectric and electrolyte materials, the mechanical and physical properties of the two materials are also blended in this region in gradient fashion, so as to reduce any stresses that may arise.

Figure 4:
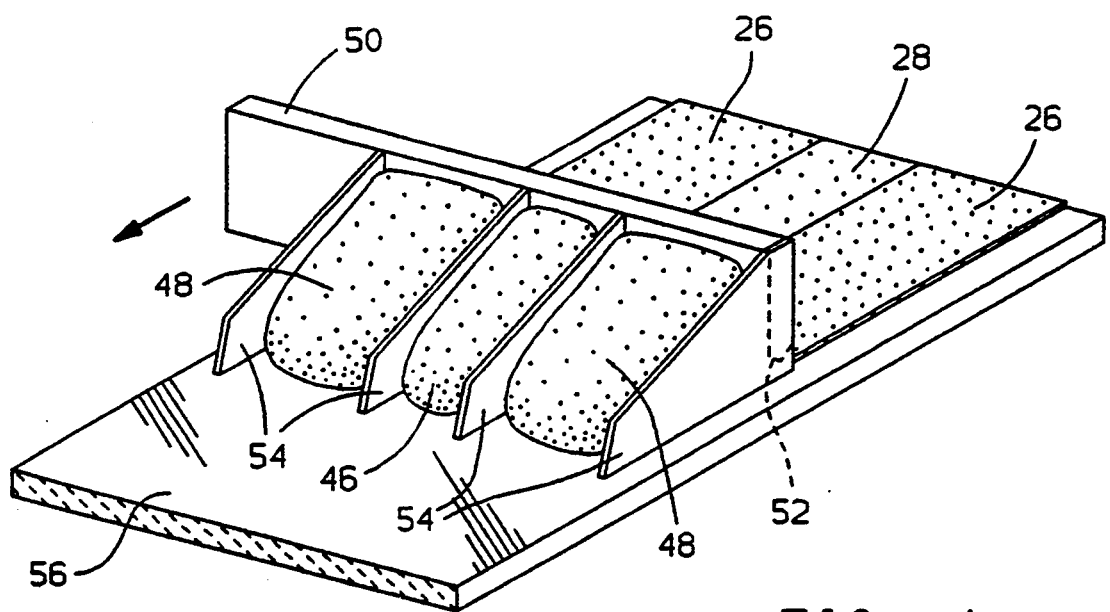
FIG. 4 illustrates a method of making a composite tile for an exhaust sensor including the step of co-depositing a dielectric composition and an electrolyte composition on a substrate using a partitioned doctor blade according to the present invention.

FIG. 4 illustrates a method of forming a composite tape according to the present invention including co-depositing a first slurry 46 including an electrolyte material; and a second slurry 48 including a dielectric material. The two slurries are co-deposited using a doctor blade 50 which may include first and second spaced apart flat legs and an elevated doctor blade knife 52 extending there between. Extending out perpendicular to the doctor blade are slurry dividers 54 for segregating the dielectric and electrolyte slurries. Preferably the tape is cast having a first compartment defined by adjacent slurry dividers for holding the dielectric slurry, a second compartment defined by adjacent slurry dividers for holding the electrolyte slurry and a third compartment defined by adjacent slurry dividers for holding the dielectric material. When the tape is cast, the tape can be cut down the middle of the electrolyte portion to provide two large tapes including a dielectric portion and an electrolyte portion. The doctor blade can be placed on a substrate such as glass 56, mylar or other flat surface, from which the casted tape can be easily removed. When the compartments are filled with the appropriate slurry, the doctor blade is advanced over the carrier or flat surface in a direction towards the slurry dividers to co-deposit or co-cast a dielectric slurry and an electrolyte slurry. The dielectric and electrolyte slurries mix to form a confluent, blended interface or transition zone including an increasing gradient concentration of electrolyte moving towards the center of the tape and an increasing concentration of dielectric material moving to the outer edges of the tape. The co-deposited or co-casted slurries are allowed to dry to form a single tape.

A suitable dielectric composition includes a dielectric powder such as alumina. The composition also includes deionized water or an organic solvent such as methyl ethyl ketone as the vehicle or medium, and organic additives, such as binders, plasticizers, and defoaming agents. The powder particle size may range from about 5 to about <0.1 micron and the powder may be present in a weight percent ranging from about 45 to about 65 of the composition. The binder may be present in an amount ranging from about 7 to about 15 weight percent of the composition and the water/solvent may be present in an amount ranging from about 28 to about 48 weight percent of the composition.

A suitable electrolyte composition includes an electrolyte material such as zirconia. The zirconia powder may have a particle size ranging from about 1 to about <0.1 micron and the zirconia may be present in about 45 to about 65 weight percent of the total composition. The composition may include an organic additives such as binders, plasticizers, and defoaming agents present in an amount ranging from about 7 to about 15 weight percent of the total composition. The composition also includes about 28 to about 48 weight percent of deionized water or solvent. The slurry process produces a thin tape that when laminated to a substrate provides the advantages of reduced thermal stress between the dielectric and electrolyte portions. By reducing the zirconia to be located only at the end of the element, the dielectric is optimized.

Figure 5:
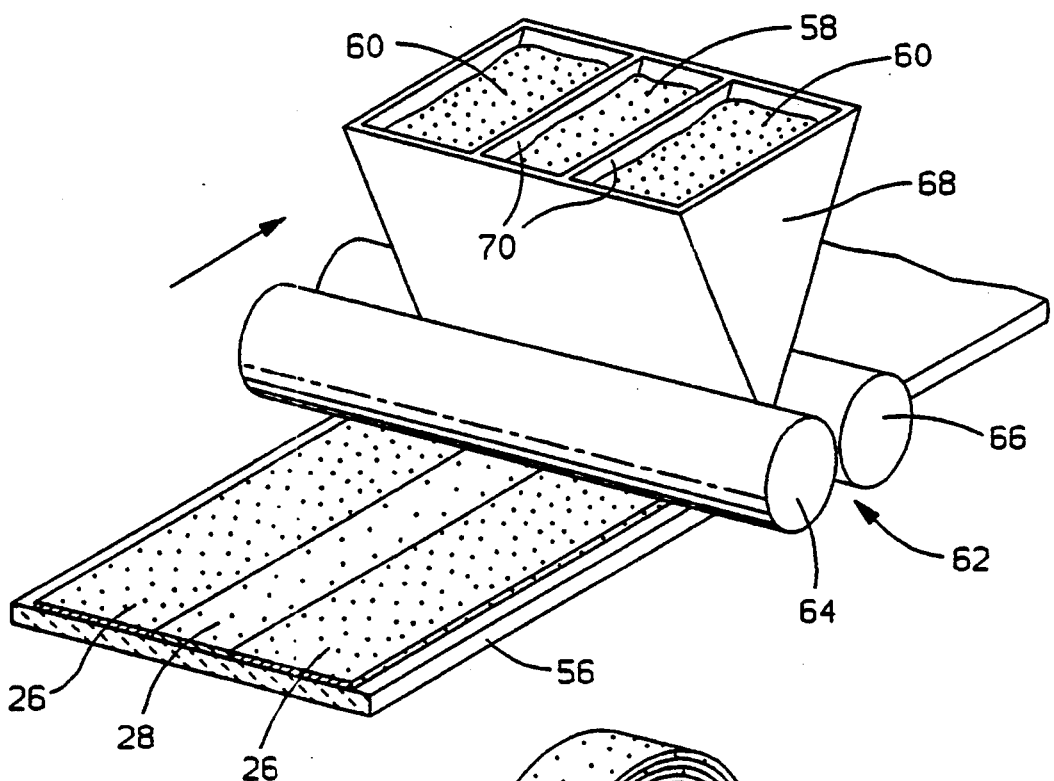
FIG. 5 illustrates a process of making an exhaust sensor substrate according to the present invention including the step of delivering an electrolyte composition and a dielectric composition to a compaction press in side by side arrangement.

FIG. 5 illustrates another method of making a flat plate oxygen sensor substrate according to the present invention. The method includes advancing an electrolyte composition 58 and a dielectric composition 60 towards a compaction press 62 to form a single tape including an electrolyte portion and a dielectric portion. The compaction press may comprise a pair of opposed rollers 64, 66 moving in opposite directions. The dielectric material and the electrolyte material may be placed in separate hoppers or a single hopper 68 including a divider 70 so that the materials may be advanced to the compaction press in a side by side relationship. The powder includes a binder such as that described hereafter with respect to FIG. 6. The compressed powder forms a tape which is then fired to form a substrate. As described above, this process will also result in a transition zone wherein there is an increasing concentration of dielectric material in a direction towards the first portion of the tape and an increasing gradient concentration of electrolyte material in a direction towards the second portion of the tape. The co-deposited or co-casted tape can then be fired to form a ceramic substrate including a first dielectric portion, second electrolyte portion, and a transition zone interposed between the first and second portions including an increasing concentration of dielectric material in the direction towards the first portion and an increasing concentration of electrolyte material in the direction towards the second portion of the substrate. The compaction press process provides all the advantages of a dry process, namely, no drying shrinkage, and no delay due to handling the tape.

Figure 6:
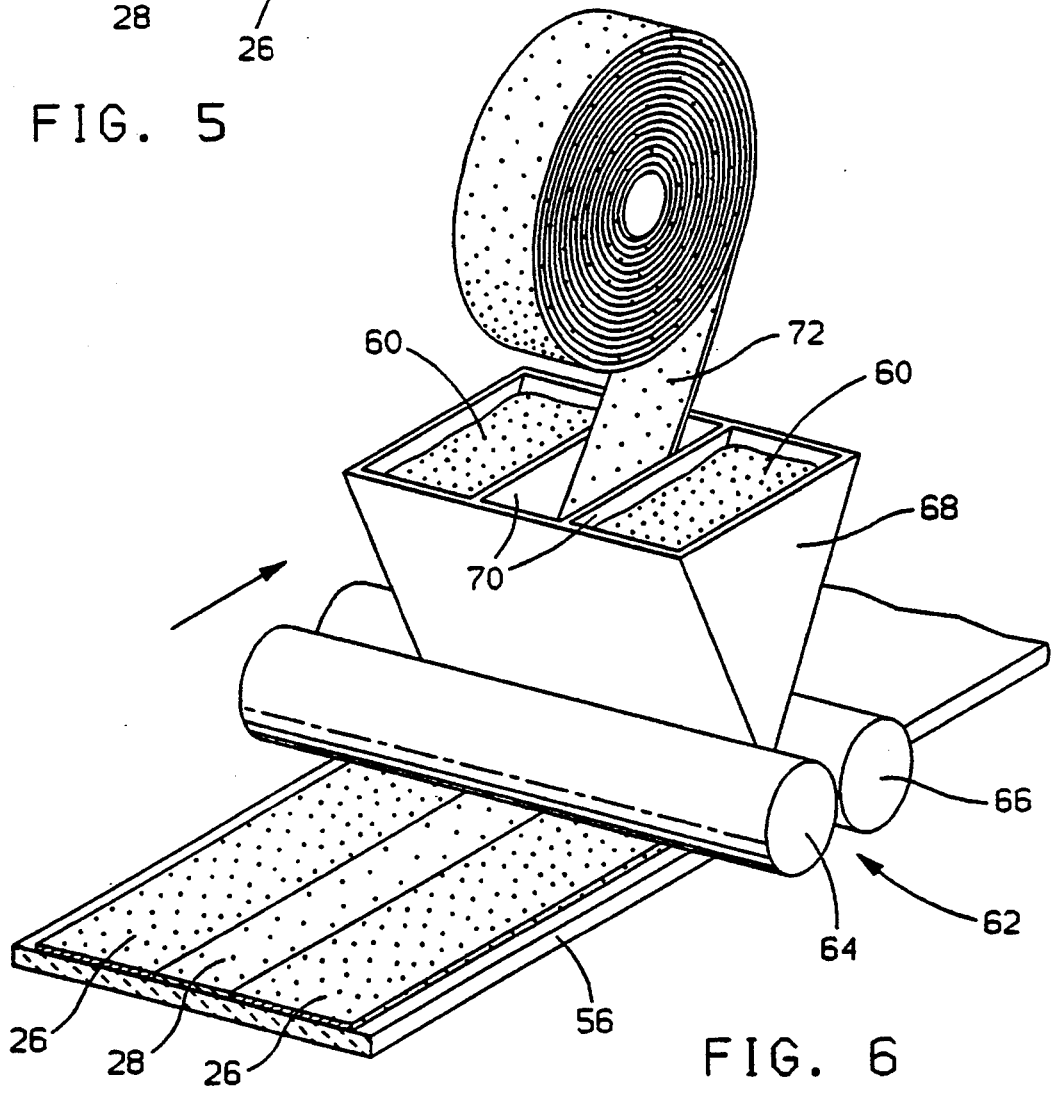
FIG. 6 illustrates a process of making an exhaust gas sensor according to the present invention including the step of delivering an electrolyte tape and a dielectric composition to a compaction press in a side by side arrangement.

FIG. 6 also illustrates another method of making an exhaust sensor according to the present invention wherein a dielectric composition 60 and an electrolyte tape 72 is fed to the compaction press 62 so that a single piece of tape emerges from the compression press including a first dielectric portion and a second electrolyte portion. The electrolyte tape is pre-made from a composition including a dry electrolyte powder such as zirconia and a well dispersed organic binder such as an acrylic polymer. The binder may be present in an amount ranging from about 7 to about 14 weight percent of the total composition. The dielectric composition may include a dielectric powder such as alumina and a well dispersed organic binder such as an acrylic polymer. The organic binder may be present in an amount ranging from about 7 to about 14 of the dielectric composition. The dielectric powder and the electrolyte powder may have a particle size ranging from about 5 to less than 0.1 micron. This process provides the advantage of being able to preform the electrolyte tape and add the dielectric subsequently.

The above-described dry compaction press process illustrated in FIGS. 5 and 6 produce a tape having a thickness ranging from about 0.003 to about 0.050 inches. In contrast, the above-described slurry process illustrated in FIG. 4 produces a thinner tape having a thickness ranging from about 0.001 to about 0.015 inches.

A calendaring process can be conducted with a partially wet electrolyte and dielectric composition each having characteristics similar to modelling clay or bread dough to produce a tape having a varying thickness ranging from about 0.002 to about 1.0 inch. The calendaring process is advantageous because of its capability to produce tapes within a much wider range of thickness.

Similarly, in FIG. 1 an outer electrode protective layer 32 can be constructed as a composite. This can be made from a dielectric material such as alumina and provides protection for both the outer electrode and the outer electrode lead. This layer 32 can be made as individual layers or can be combined as is shown in FIG. 1. By combining the two dissimilar tapes, into a composite structure, part handling and alignment concerns are minimized resulting in lower cost and higher quality.

The outer electrode protective layer has a first portion 36 with open porosity so that the exhaust gas may be sufficiently sampled. Its chief function is to provide protection for the outer electrode against particulate abrasion and to act as a barrier against exhaust gases that may be harmful or degrade the performance of the outer electrode, such as silicon or lead, etc. The porosity in the alumina material may be controlled by organic additives such as corn starch, which upon sintering, leave pores in the ceramic structure, or by careful selection of the particle size of the originating raw materials.

The outer electrode lead protective layer 34 only has the requirement of high density. The density is controlled by controlling the various parameters in the manufacture of the tape, such as particle size distribution, surface area, chemistry, binder and other additives. The protective layer 32 including a high density portion 34 and an open porosity portion 36 can be formed by the co-casting steps of the present invention.

The embodiments of the invention in which an exclusive property or privilege is claimed as defined as follows:

1. An exhaust gas sensor comprising:
   a substrate having a first dielectric portion, a second electrolyte portion, and a transition zone interposed between the first and second portions comprising a dielectric material having an increasing gradient concentration in the direction towards the first portion of the substrate, and an electrolyte material having an increasing gradient concentration in a direction towards the second portion of the substrate; and an outer electrode on one face of the substrate and an inner electrode on the other face of the substrate.

2. An exhaust sensor as set forth in claim 1 wherein said electrolyte material and said electrolyte portion each comprise zirconia.

3. An exhaust sensor as set forth in claim 1 wherein said dielectric material and said dielectric portion each comprise alumina.

* * * * *